(12) United States Patent
Scholz et al.

(10) Patent No.: US 6,248,085 B1
(45) Date of Patent: Jun. 19, 2001

(54) SURGICAL PREP SOLUTION DISPENSER AND METHOD

(75) Inventors: Matthew T. Scholz, Woodbury, MN (US); Dennis L. Baker, Houlton, WI (US); Robert P. Zaspel, St. Paul, MN (US); Jon A. Kirschhoffer, White Bear Lake, MN (US); Maurice H. Kuypers, Stillwater, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/237,741

(22) Filed: Jan. 26, 1999

Related U.S. Application Data (63) Continuation-in-part of application No. 09/016,046, filed on Jan. 30, 1998, now abandoned.

(51) Int. Cl.$^7$ .............................. A61M 35/00; B43K 5/04; B05C 11/00; B65D 83/10
(52) U.S. Cl. ............................... 604/2; 118/266; 118/270; 401/152; 206/361
(58) Field of Search ........................... 604/1–3, 295–301; 118/264, 266, 270; 401/121, 125, 127, 152; 215/220, 386, 390; 206/210, 361, 363

(56) References Cited

U.S. PATENT DOCUMENTS

| | | |
|---|---|---|
| 185,693 | 12/1876 | Newton . |
| 402,326 | 4/1889 | Hoerle . |
| 473,025 | 4/1892 | Seward . |
| 541,593 | 6/1895 | Cole . |
| 701,911 | 6/1902 | Millar . |
| 1,098,976 | 6/1914 | Rosenstein . |
| 1,645,159 | 10/1927 | Russell . |
| 2,754,821 | 7/1956 | Burbig et al. ..................... 128/249 |

(List continued on next page.)

FOREIGN PATENT DOCUMENTS

| | | |
|---|---|---|
| 0 375 579 | 6/1990 | (EP) . |
| 490500 | 4/1919 | (FR) . |

OTHER PUBLICATIONS

"Prevail—The New Choice in Preop Prep", Allegiance, 1998.

Primary Examiner—Dennis Ruhl
(74) Attorney, Agent, or Firm—John A. Burtis (57) ABSTRACT

An apparatus or kit for applying a predictable amount of liquid such as a surgical prepping solution to an applicator having a resilient, porous pad. The apparatus includes a receptacle having an internal space such that when the pad is placed within the space, the pad is compressed to a predetermined degree. The receptacle is attached to a bottle or other container holding surgical prepping solution. In one embodiment, a dip tube extends from an inlet near the bottom of the bottle to an outlet positioned within the internal space of the receptacle. Most preferably, the outlet extends into the internal space of the receptacle. Pressurizing the bottle dispenses liquid through the dip tube onto the applicator. A method of use of the kit or apparatus is also disclosed.

42 Claims, 5 Drawing Sheets

U.S. PATENT DOCUMENTS

| | | | |
|---|---|---|---|
| 2,774,093 | 12/1956 | King | 15/123 |
| 3,146,806 | 9/1964 | Ginsburg . | |
| 3,261,355 | 7/1966 | Burbig | 128/249 |
| 3,262,461 | 7/1966 | Kambersky . | |
| 3,529,899 | 9/1970 | Gruska . | |
| 3,759,259 | 9/1973 | Truhan . | |
| 4,341,231 | 7/1982 | Costa . | |
| 4,365,642 | 12/1982 | Costa . | |
| 4,507,111 | 3/1985 | Gordon et al. . | |
| 4,578,055 | 3/1986 | Fischer . | |
| 4,747,719 | 5/1988 | Parkin . | |
| 4,854,760 | 8/1989 | Pike et al. . | |
| 4,995,344 | 2/1991 | Olson . | |
| 5,037,226 | 8/1991 | Davis et al. . | |
| 5,120,301 | 6/1992 | Wu . | |
| 5,266,266 | 11/1993 | Nason . | |
| 5,308,180 | 5/1994 | Pournoor et al. . | |
| 5,332,325 | 7/1994 | Crosnier et al. . | |
| 5,433,782 | 7/1995 | Filbert et al. . | |
| 5,599,125 | 2/1997 | Vasas et al. . | |
| 5,658,084 | 8/1997 | Wirt . | |
| 5,661,865 | 9/1997 | Humphrey . | |
| 5,713,843 | 2/1998 | Vangsness . | |
| 5,795,343 * | 8/1998 | Yavitz et al. | 604/310 |

\* cited by examiner

SURGICAL PREP SOLUTION DISPENSER AND METHOD

RELATED APPLICATIONS

This application is a continuation-in-part of U.S. patent application Ser. No. 09/016,046, filed Jan. 30, 1998, now abandoned.

TECHNICAL FIELD

The invention relates generally to the application of surgical prepping solutions to the body, and more specifically to an apparatus and method for dispensing the solution into an applicator in a controlled manner.

BACKGROUND OF THE INVENTION

Antiseptic preparation of patients for surgery conventionally includes a 3–10 minute scrubbing of the affected area with an antimicrobial soap solution followed by the application of a water-soluble antiseptic paint solution. The solutions are conventionally applied with saturated gauze or sponges that are attached to a handle or held with forceps. The sponges are saturated by soaking in open pans of solution.

This procedure has the drawback that the solution can drip and pool unseen in locations hidden by the patient's body. Pooling of the antimicrobial solution can result in skin irritation and even chemical burns if strong iodine solutions are employed. Furthermore, it is desirable to prevent pooling of flammable antiseptics, such as those based on alcohol/water solutions.

One way of dealing with this drawback is to provide the solution in a sealed ampoule within an applicator. For example, co-assigned U.S. Pat. No. 5,658,084 "Liquid applicator with frangible ampoule and support" describes such an applicator. While providing clean and efficient dispensing, such an applicator is somewhat expensive to provide.

A less expensive expedient is to provide an applicator having a sponge and a handle within a sealed pouch that also contains a free quantity of prepping solution. For example, the E-Z Preps product commercially available from Becton Dickinson and Company, Franklin Lakes, N.J., provides two eight-inch sponge sticks immersed in Povidone-iodine topical solution. The sponges are supplied presaturated with excess solution that distributes freely within the pouch, completely coating the handle. Therefore, these applicators are messy to use in practice.

SUMMARY OF THE INVENTION

This invention provides a kit or apparatus for applying surgical prepping solution to a patient. The invention facilitates loading an inexpensive applicator with an adequate, but substantially dripless dose of solution immediately before use from a liquid container. Preferably, the liquid container is a bulk container holding multiple doses of solution, e.g., at least 10 and preferably at least 20 doses.

Liquid loading is controlled by filling a resilient porous applicator pad in a semi-compressed state. As the applicator pad is removed it expands ensuring that the antimicrobial solution occupies no more than the saturation level of the pad in order to minimize dripping. Alternatively, the applicator pad could be filled in the applicator in a non-compressed state and pulled or pushed through a narrow opening that compresses to wring or squeeze excess solution from the pad. It is preferred that the applicator pad be resilient to allow for compression and subsequent expansion. In this manner, by controlling the amount of compression the amount of liquid impregnated into the applicator pad may be precisely controlled for any given substrate material.

The pad contracts and expands between a compressed or semi-compressed state and an uncompressed state, and the pad is capable of holding more surgical prepping solution in its uncompressed state than in its compressed or semi-compressed state. Surgical prepping solution may saturate the pad in its compressed or semi-compressed state, but will be held by the pad at less than a saturation level when the pad is not compressed.

Generally, a kit of the invention comprises an applicator having a resilient, porous pad attached to a handle, a bottle for a surgical prepping solution, and a receptacle attached to the bottle. The receptacle defines an internal space having a size relative to the pad such that when the pad is placed within the space, the pad is compressed to a predetermined degree. A passageway extends between the bottle and the internal space of the receptacle through which surgical prep solution can flow from the bottle into the internal space to load the pad with surgical prepping solution.

In a second aspect of the invention, the kit generally comprises an applicator having a resilient, porous pad attached to a handle, and a receptacle adapted to be attached to a bottle of surgical prepping solution. The receptacle defines an internal space having a size relative to the pad such that when the pad is placed within the space, the pad is compressed to a predetermined degree. A passageway is provided into the internal space of the receptacle through which surgical prep solution can flow from a bottle attached to the receptacle into the internal space to load the pad with surgical prepping solution.

Preferably, an inlet or dip tube extends from the receptacle into the bottle, the dip tube defining the passageway as having an inlet near the bottom of the bottle. Most preferably, the dip tube also extends into the internal space of the receptacle, and has outlet openings or slots into the internal space along the sides of the dip tube. The outlet openings or slots help prevent blockage of surgical prepping solution by the compressed material of the pad. These outlet openings or slots constitute one preferred means for preventing blockage of solution. Other embodiments of such means include providing a stop in the internal space to limit insertion of the pad into the internal space, or in some applications having the handle extend all the way through the pad to provide a stop function.

In a third aspect of the invention, an apparatus is provided generally comprising a receptacle having an internal space such that when the pad is placed within the space, the pad is compressed to a predetermined degree, a bottle containing surgical prepping solution, and an inlet tube extending into the internal space. The inlet tube defines a passageway in fluid communication with the bottle for dispensing surgical prepping solution into the pad while the pad is within the receptacle. The inlet tube has outlet slots into the internal space along the sides of the inlet tube.

In at least one embodiment, the receptacle is releasably attached to the bottle. This facilitates reuse of the receptacle with multiple bottles.

In at least one embodiment the receptacle is disposable and may be provided to the customer with the pad preloaded and precompressed within the disposable receptacle.

In one preferred embodiment a reusable receptacle is used along with an applicator pad that is sealed into a preferably sterile disposable plastic package. The receptacle further comprises one or more spikes that pierce the applicator pad as the applicator is inserted into the receptacle. Preferably, the applicator handle is provided with a slot within the pad such that the spike enters the slot.

Preferably, the pad is sized and configured relative to the internal space so that the pad is compressed within the receptacle to between 40–90% of its non-compressed post-wetting volume. Most preferably, this compression is between 60–80% of the pad's non-compressed post-wetting volume. Also, preferably, the entire pad is compressed within the internal space of the receptacle.

In one preferred aspect of the invention, the pad further includes a binder holding the pad in a compressed configuration before the pad is inserted in the receptacle. The binder dissolves, erodes, swells or otherwise releases after the pad is loaded with surgical prepping solution to allow the pad to expand after it has been loaded with surgical prepping solution.

Most preferably, the pad has a generally polyhedron configuration with two generally parallel major surfaces. The handle is elongate and extends from the pad in a direction generally parallel to the two major surfaces. The internal space of the receptacle has a polyhedron configuration corresponding to the configuration of the pad but smaller than the pad so that the pad is compressed when it is inserted in the internal space.

Also preferably, a flared opening is provided in the receptacle to the internal space.

Conveniently, a cap is provided for releaseably sealing the opening in the receptacle. The cap is preferably connected to the receptacle to avoid complete separation and possible loss of the cap. For example, a tether may hold the cap to the receptacle, or a hinge pivotably may connect the cap to the receptacle.

Also, in another aspect of the invention, the bottle and receptacle are blow or vacuum molded or thermoformed in one integral piece.

Most preferably, the handle is inserted in the pad a distance of at least 75% of the length of one of the dimensions of the pad.

In preferred embodiments, the applicator can be as simple as a handle attached to a resilient pad. The dispensing apparatus makes such a simple and inexpensive applicator work to best advantage. Conveniently, the dispensing means is a bottle for containing the liquid, the bottle having some means for attaching the receptacle to the bottle. The bottle is provided with a dip tube with an inlet near the bottom of the bottle and an outlet adjacent the attachment for the receptacle. Most preferably, the dip tube is mounted on the receptacle such that when the receptacle is placed on the bottle the inlet is near the bottom of the bottle. Pressurizing the bottle, for example by squeezing, dispenses liquid through the dip tube into the applicator. Alternatively, the bottle could be pressurized by other mechanical means, such as a treadle, or other expedients, such as compressed gas.

In a fourth aspect, the invention provides a method of preparing a patient for surgery, the method comprising the steps of:

(a) providing an applicator having a resilient, porous pad, and an apparatus comprising:
   a receptacle having an internal space such that when the pad is placed within the space, the pad is compressed to a predetermined degree; and
   a passageway into the receptacle for dispensing a surgical prepping solution onto the pad while the pad is within the receptacle;

(b) inserting the pad into the internal space of the receptacle, and compressing the pad to a predetermined degree within the internal space;

(c) passing surgical prepping solution through the passageway into the internal space of the receptacle to wet the pad with a surgical prepping solution using the dispensing means;

(d) withdrawing the pad from the receptacle such that the pad expands sufficiently so that the surgical prepping solution occupies less than the saturation level of the pad; and (e) painting the surgical prepping solution onto the patient with the applicator.

Preferably, the pad is compressed within the receptacle to between 40–90% of the pad's non-compressed post-wetting volume. Most preferably, the pad is compressed within the receptacle to between 60–80% of the pad's non-compressed post-wetting volume.

Also, in one aspect of the method, the pad is held in a compressed configuration with a binder before the pad is inserted in the receptacle, and the binder is dissolved, eroded, swelled or otherwise released by the surgical prepping solution to allow the pad to expand after it has been loaded with surgical prepping solution to prevent reuse of the pad in internal space of the receptacle.

Excess solution in the receptacle after use may be allowed to flow back into the bottle if that is desired. This may be facilitated by vacuum created in the bottle, for example, when the bottle recovers from being squeezed.

These and other features and advantages of the invention will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
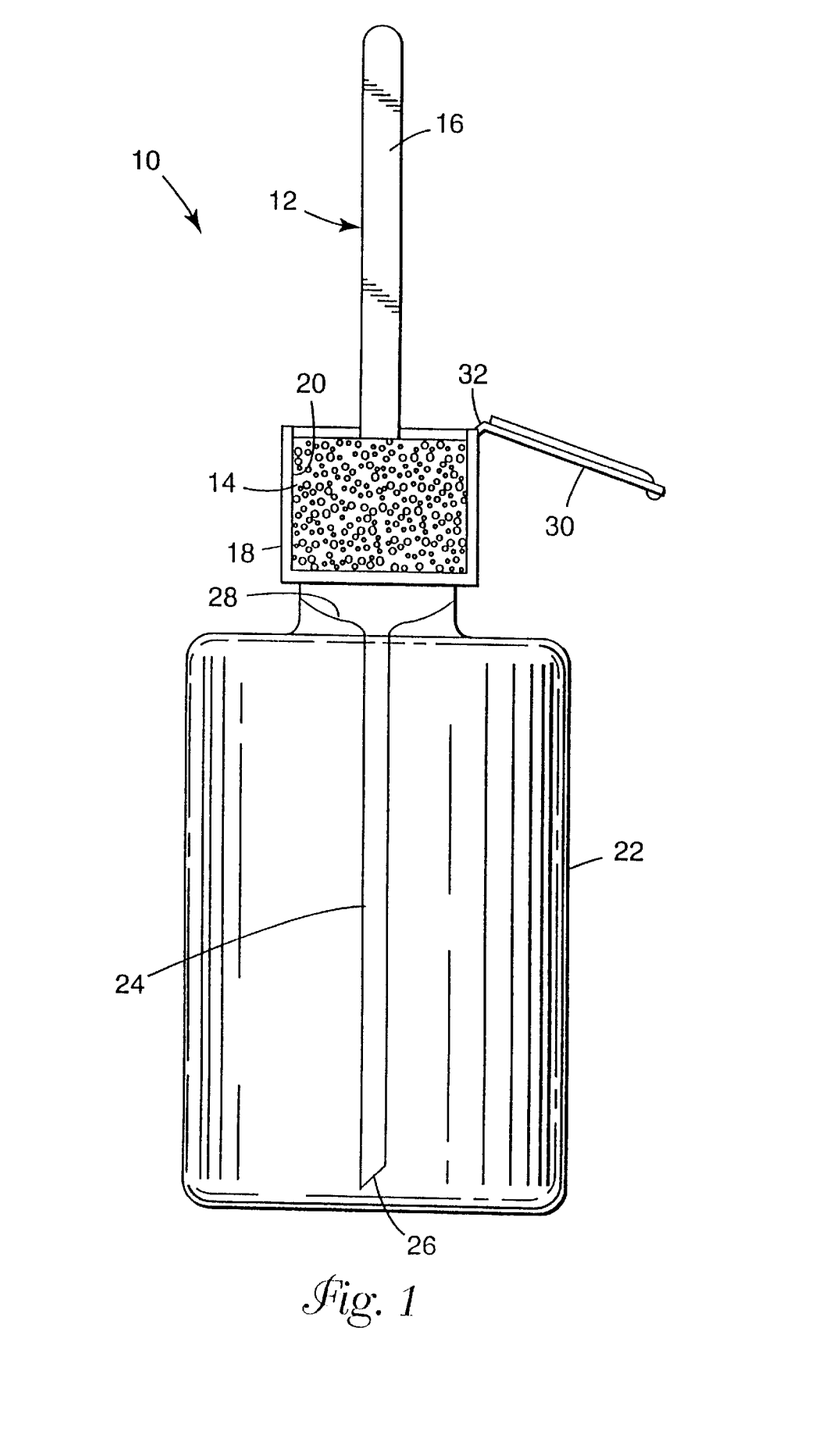
FIG. 1 is a front view of an apparatus according to an embodiment of the present invention.
Figure 2:
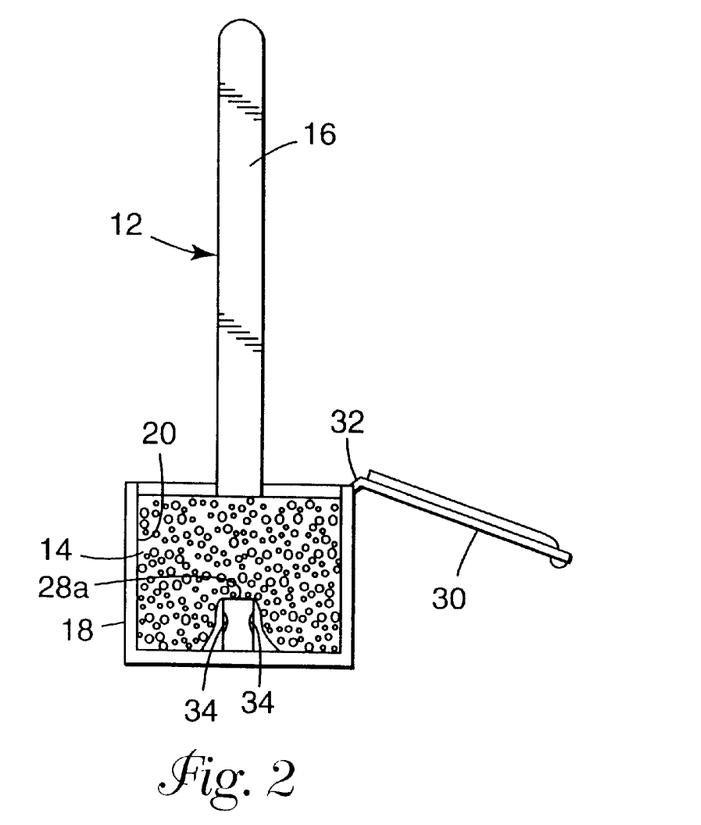
FIG. 2 is a detail view of an alternate embodiment.
Figure 3:
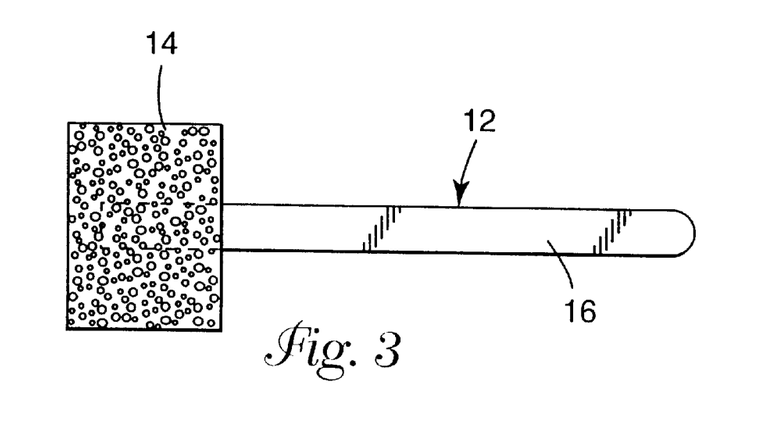
FIG. 3 is a front view of a preferred applicator used in a kit of the invention.

Referring now to FIG. 1, a front view of an apparatus 10 according to an embodiment of the present invention is illustrated. The apparatus 10 is used with an applicator 12 (e.g., see FIG. 3) having a resilient, porous pad 14 and, most conveniently, an elongate handle 16. The apparatus includes a receptacle 18 having an internal space 20 such that when the pad 14 is placed within the space, as illustrated in FIGS. 1 and 2, the pad 14 is compressed to a predetermined degree along one or more axes.

The apparatus 10 also includes a means for dispensing liquid onto the pad 14 while the pad is within the space 20 in the receptacle 18. In the illustrated embodiment, this means is a bottle 22, which conveniently has a dip tube 24 leading from an inlet 26 near the bottom of the bottle to an outlet 28 adjacent the receptacle 18. When the interior of the bottle 22 is pressurized, liquid within the bottle is forced through the dip tube 24 to the receptacle. Preferably, the inlet 26 is angled or tapered to prevent binding of the inlet by contacting the bottom of bottle 22. Alternatively, a plurality of openings (not shown) can be formed in the dip tube 24 adjacent the lower or inlet end. The bottle 22 can be pressurized in any number of ways, for example it can simply be squeezed by hand, or it could be pressurized by a separate tube from a pneumatic foot treadle.

To use the apparatus, the applicator 12 is positioned with its pad 14 within the space 20, and the bottle 22 is pressurized. The wetting of the pad 14 is preferably monitored while this is occurring. To make this easier, it is convenient to make at least a portion of the receptacle 18 transparent or translucent so that the wetting of the pad can be observed in side view. Visualizing the wetting of the pad 14 is usually not difficult when the apparatus 10 is being used to dispense surgical prepping solutions, as many of the most popular solutions are strongly colored by iodine containing compounds. Prepping solutions that are not naturally colored may optionally incorporate dyes or colorants compatible with the antimicrobial solution.

Then the applicator 12 is removed from the receptacle 18. The dimensions and materials are sized so that upon such removal, the pad recovers from its compression under its own resilience, holding a dose of liquid preferably very close to its saturation level for holding liquid without significant dripping. As used herein, the term "saturation level" means the maximum liquid capacity a pad may hold without dripping when held in a filled state in a horizontal position (e.g., for a polyhedron applicator pad, with one of its major surfaces held parallel to the ground, and for a cylindrical, conical or frustaconical pad with the major axis held parallel to the ground) for 20 seconds.

It may be convenient to attach the receptacle 18 to the bottle 22 permanently, but it may also be convenient to provide a means for releasably attaching the receptacle to the bottle. This is easily accomplished by threads, by snap fitting components, by taper locking components, or other expedients that will occur to the skilled artisan. When actually producing the apparatus 10 for commercial use, it may be convenient to package the receptacle 18 with the bottle 22 and provide for a more permanent connection.

Alternatively, it may be convenient to package a single-use receptacle 18 with each applicator 12, so that the receptacle is brought or fitted onto the dispensing means only just before use. In such cases, ease of quick attachment and release will be more important in choosing which means for attaching the receptacle 18 is most suitable.

Preferred materials useful for forming the pad 14 of the present invention are open-cell foams such as polyurethanes including polyurethane foams based on alliphatic and aromatic isocyanates and polyester or polyether polyols. These polyurethane foams may also be filled with fillers including fibrous fillers and may be colored using pigments or dyes. These foams may also optionally contain absorbent polymers, such as supersorbers. Other foams include cellulose and natural foams as well as those based on polyvinyl alcohol, ethylene vinyl acetate, polymers of unsaturated monomers including but not limited to acrylates, methacrylates, n-vinyl lactams, acrylamides, styrene, and the like. Other useful substrates include resilient non-woven pads such as carded or blown microfiber mats.

Preferably, the applicator pad and any binder present may be sterilized by conventional methods such as steam, ethylene oxide or irradiation without adverse effects on the substrate's physical properties or toxicity. The applicator pad may be of any geometry but is preferably easy to place into the solution dispenser and has a major surface that is convenient for painting the antimicrobial solution onto the skin of the patient. Therefore the applicator pad is preferably polyhedron (e.g. wherein all faces are parallelograms, cuboidal, prismatic, etc.), cylindrical or conical. Most conveniently the applicator pad has a simple geometry having two major surfaces such as a box or disk shape. The applicator pad may have a handle preattached or may be used along with forceps or other suitable means.

While surgical prepping solutions are strongly bactericidal by definition, one should always strive to minimize contamination and cross-contamination between patients. This concern may arise, for example, with respect to solutions that do not contain a high level of alcohol or are known to harbor resistant bacteria. Some expedients are possible to reduce this concern. A simple precaution is to provide a cover 30 for the receptacle 18, which may conveniently be attached by a standard hinge or a molded-in living hinge 32. Another expedient, discussed above, is to provide a disposable receptacle or receptacle insert with each applicator. Yet another expedient is to provide applicators where the pad expands significantly beyond its pre-wetted volume after wetting with the surgical prepping solution. In this manner, it is extremely inconvenient to place a used applicator back into the device thus ensuring aseptic technique is maintained. This may be accomplished by two methods:

1. Swelling of the foam structure due to uptake of the surgical prepping solution. This has been observed, for example in polyurethane foam, commercially available as foam P-90 (90 pore/in) from Illbruck Co. of Minneapolis, Minn., after is has been exposed to an isopropyl alcohol based surgical prepping solution commercially available as Duraprep™ from 3M Company of St. Paul, Minn.
2. Use of a resilient applicator pad that is precompressed and held in the precompressed state by a binder that is rapidly soluble, swellable, erodable or otherwise rapidly releases in the antimicrobial solution allowing the pad to expand. For example, if a polyurethane foam sponge is lightly impregnated with a suitable binder solution, s compressed and dried in the compressed state the binder will maintain the compressed state. Once the sponge is exposed to the antimicrobial solution, however, the binder will dissolve, swell, or otherwise lose integrity and the foam will rapidly expand. In this case the dispenser device will prevent complete expansion before removal and ensure that the applicator pad expands further upon removal thus delivering an impregnated but drip free pad.

Suitable binders preferably dissolve, swell, or otherwise loose integrity rapidly in the antimicrobial solution such that the applicator pad swells in less than 60 sec, preferably less than 30 sec and most preferably in less than 15 sec. Suitable binders will vary depending on the antimicrobial solution employed and particularly depending on the solvent system of the antimicrobial solution.

For aqueous and hydroalcoholic solutions suitable binder may include: natural polymers such as starch and cellulose derivatives, proteins such as gelatin, collagen, casein, albumin etc., polysaccharides such as agar, dextrin, various gums (xanthan gum, gum arabic etc.) and may include small molecules such as sucrose. Synthetic polymers may also be useful such as those derived from vinylic unsaturated monomers including, acrylates, methacrylates, vinyl acetate and its hydrolyzed derivatives, styrene and styrene derivatives such as styrene sulfonate, N-vinyl lactams, vinyl phosponate, acrylamides, and the like. Co-polymers of some of these monomers will also be suitable. Other synthetic polymers may also be useful including polyethylene oxide and EO/PO copolymers that are waxes at room temperature, soluble or swellable polyurethanes, surfactants that are waxes at room temperature such as those based on PEG, and the like. Polymers incorporating ionic groups and large proportions of hydrophilic monomers are particularly preferred in order to ensure rapid dissolution/swelling in the polar solvents typically employed in antimicrobial solutions.

Depending on the density and pore structure of the applicator pad the amount of compression can vary widely. Operating room nurses, however, are accustomed to using applicator pads that are approximately 2"×2"×1" (width) and need to have these pads impregnated with 15–40 ml of solution. For pads of this size delivering the required amount means that the pad should be compressed to between 40–90% of their non-compressed post impregnation volume as measured immediately upon impregnation and removal from the dispenser, and more preferably between 60–80%. The key requirement is that the applicator pad be impregnated with enough antimicrobial solution that the solution is easily applied to the patient to obtain a uniform coating while not so much that rapid dripping results. For applications other than the operating room other sizes may be appropriate. For example, for disinfection of IV sites a smaller size may be desired, e.g. 5–20 ml of solution may be appropriate. It has been noted that best results are obtained when the stick handle on the sponge is positioned at least 75% of the way through the sponge and preferably 80 to 95% through the sponge but may be positioned 100% through the sponge; this greatly facilitates insertion of the applicator into receptacle.

The dispensing means may be single use but is preferably reusable, e.g. as many as 40 times or more. For example, a one liter bottle may deliver 40 precisely metered 25 ml doses to 40 individual applicator pads. As mentioned above, for aseptic reasons, the applicator pads are not reused. While the depicted embodiment is particularly convenient, the applicator pad may be placed into the receptacle in any suitable orientation. The applicator pad may be placed into the dispenser in a precompressed state, e.g. using a binder, compressed as it is inserted, compressed by the action of the dispenser, compressed as it is removed from the dispenser, or combinations of these actions.

Referring now to FIG. 2, a detail view of an alternate embodiment of the apparatus 10 is illustrated. In this detail view, the dip tube 24 has a protruding outlet 28a that extends into space 20. When the bottle is pressurized, liquid enters space 20 through slots 34 on the sides of the outlet 28a. It has been observed that with some types of pads and outlet geometries, it is possible to insert the applicator 12 into the receptacle 20 with such force that the outlet 28 of FIG. 1 is partially blocked by the pad and the applicator pad is wetted only with difficulty when the bottle 22 is pressurized. As FIG. 2 illustrates, this possibility can be relieved by the use of a protruding outlet 28a. Even if the pad is inserted with excessive force, it still must deform around the protruding outlet 28a, leaving access for the liquid in the region adjacent slots 34.

Figure 4:
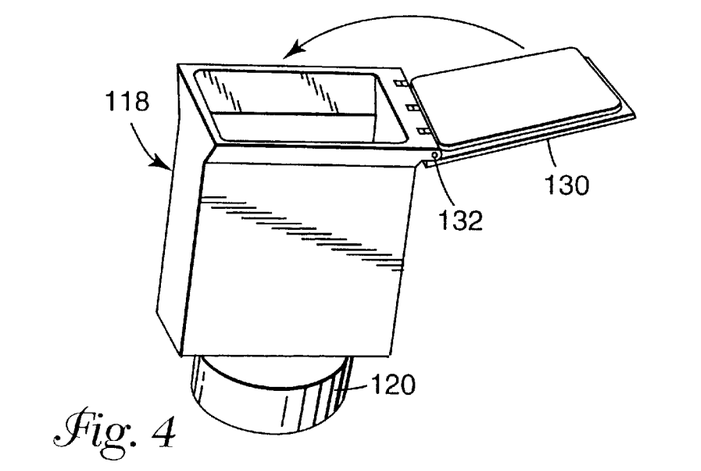
FIG. 4 is a perspective view of an alternate embodiment of the receptacle of the invention.

FIGS. 4–7 illustrate various alternative forms of the receptacle of the invention. FIG. 4 illustrates a receptacle 118 provided with a hinge 132 extending along the width of the receptacle 118, and a lid or cap 130 mounted on the receptacle by the hinge 132. Alternatively, the hinge may be provided along the length of the receptacle. The hinge 132 may be, for example, a living hinge or may take the form of interlocking crenations (projections alternating with notches) along the cap 130 and receptacle 118 with an axle passing through the crenations to pivotably lock the cap 130 on the receptacle 118. The receptacle 118 may be provided with a suitable means for mounting on a bottle, such as an annular threaded portion 120.

Figure 5:
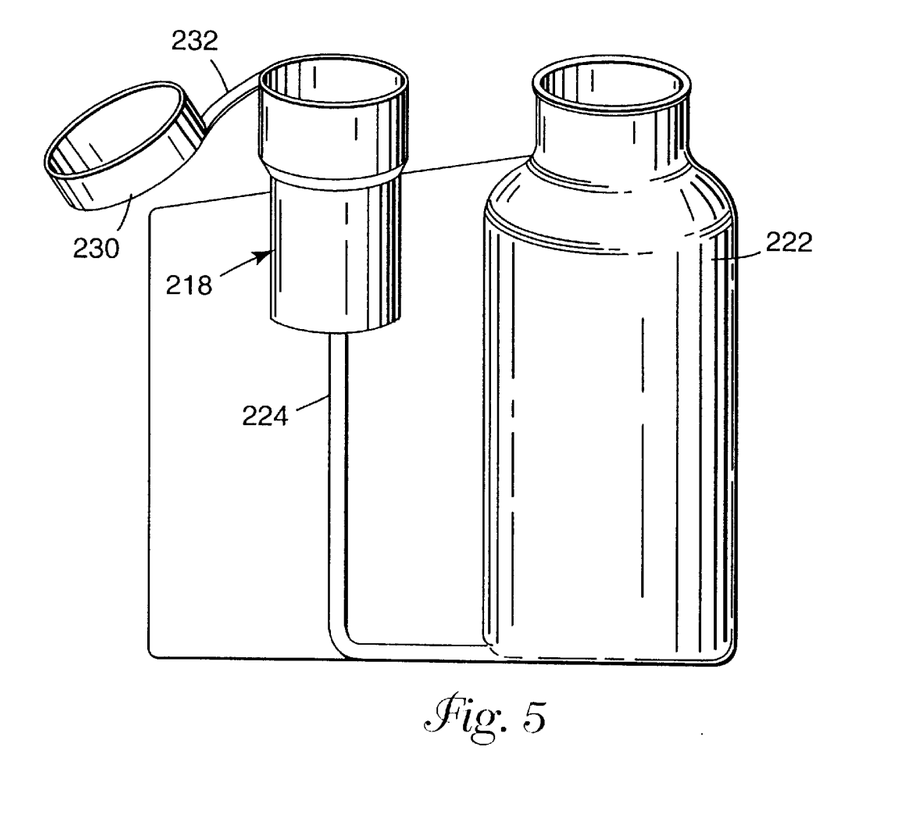
FIG. 5 is a perspective view of yet another embodiment of the receptacle and bottle of the invention.

FIG. 5 illustrates a bottle 222 and receptacle 218 integrally molded, for example, by vacuum or blow molding, or thermoforming. In this embodiment, the dip tube 224 is preferably provided along one side of the bottle 222 rather than passing through center of the bottle 222. The cap 230 of this embodiment may be connected to the receptacle 218 by a tether 232. It is contemplated with this embodiment as well as several of the other preferred embodiments discussed herein that the bottle and receptacle be formed by a blow-fill-seal or mold-fill-seal process.

Figure 6:
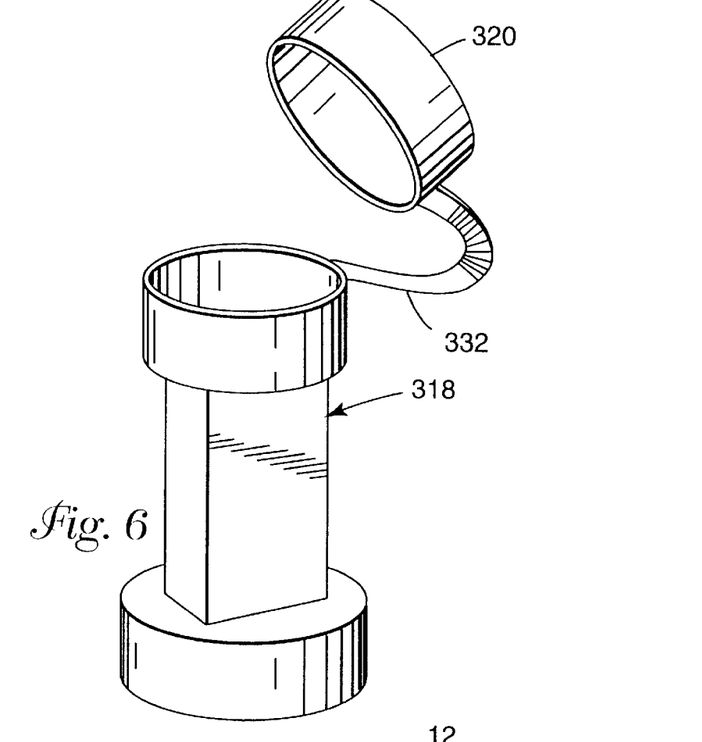
FIG. 6 is a perspective view of yet another embodiment of the receptacle of the invention.

FIG. 6 illustrates another embodiment of the receptacle 318 of the invention, in which a cap 320 is connected to the receptacle by a tether 332. In this embodiment, the cap 320 is illustrated as being adapted fitting within the end of the receptacle 318 to seal the internal space of the receptacle 318 rather than as fitting over the end.

Figure 7:
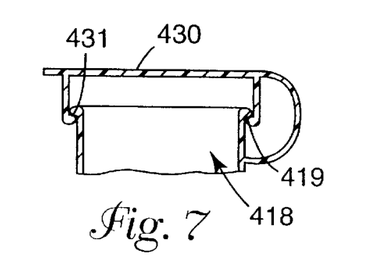
FIG. 7 is a vertical cross sectional view of yet another embodiment of the invention, illustrating details of a portion of a receptacle and a cap tethered to the receptacle.

FIG. 7 illustrates yet another embodiment of the receptacle 418 of the invention in which a cap 430 and receptacle 418 are provided with interlocking undercuts 431 and 419 to help seal the cap 430 over the opening into the internal space of the receptacle 418. Alternatives to the interlocking undercuts 431 and 419 include providing an O-ring in an annular groove (not shown) along either the male or female side of the connection between the cap and receptacle to seal the cap with respect to the receptacle.

Figure 8:
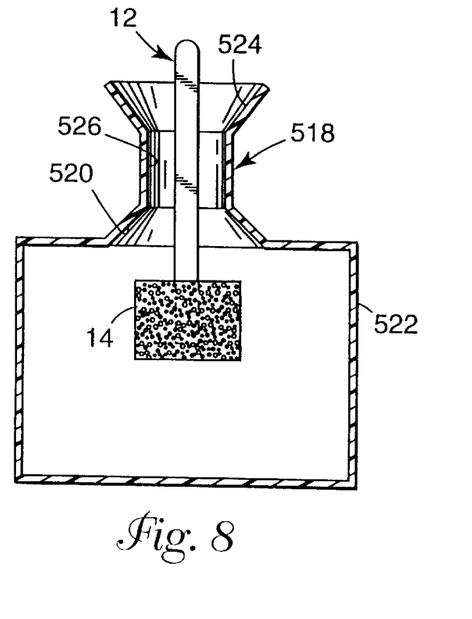
FIG. 8 is a vertical cross section of yet another embodiment of the invention.

FIG. 8 illustrates yet another embodiment of the invention in which the internal space 520 of the receptacle 518 is in the form of a passageway 520 between a prepping solution reservoir 522 and the outside. The passageway 520 is configured and sized to compress the pad 14 of the applicator 12 by a predetermined amount selected to prevent dripping of the pad 14. The passageway 520 is shown as having tapered openings 524 and 526 to facilitate insertion and retraction of the pad 14 of the applicator. The tapered opening 524 may preferably be applied to any of the embodiments of the receptacle of this invention.

Alternatively, a permanent receptacle can be used in conjunction with a disposable containment means for containing the applicator pad and a predetermined amount of prepping solution. Preferred embodiments incorporating such a containment means are shown in FIGS. 9–10.

Figure 9:
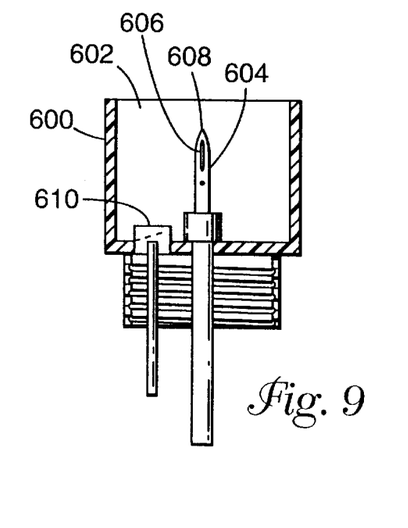
FIG. 9 is a cross section view of yet another embodiment of the invention, illustrating a receptacle further comprising a spike.

FIG. 9 illustrates a receptacle 600 having an internal space 602 in which one or more spikes 604 (preferably one) extend vertically upwardly from the bottom of the internal space 602. The spike 604 includes one or more openings 606 preferably adjacent the tip 608 of the spike 604, which open into a passageway similar to the passageways described with respect to the above described embodiments. The openings may alternatively be positioned at any point along the spike. A valve/fluid return passageway 610 is provided for returning to the bottle solution that is not carried away by the applicator.

Preferably, the spike 604 does not extend beyond the internal lumen of the receptacle, with the tip preferably well below the brim of the receptacle. This reduces the chance of inadvertent contact with the tip of the spike. Also, preferably, a cap (not shown) is provided on the receptacle 600, or a tip seal (not shown) is provided on the tip of the spike 604. A retractable tip seal (not shown) could also be provided.

Figure 10:
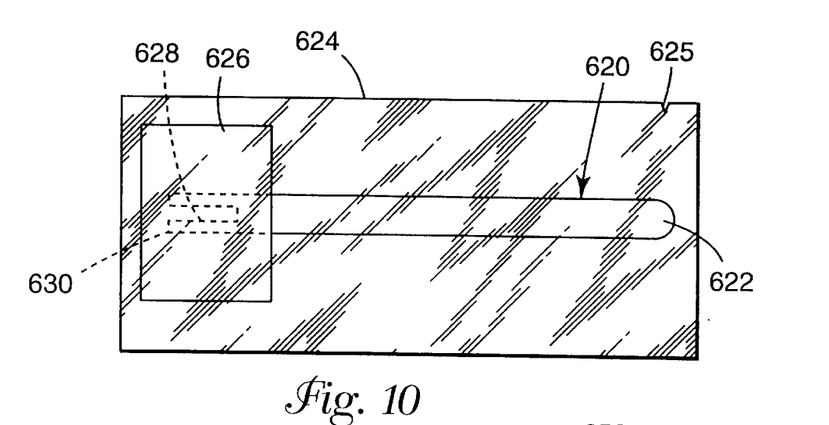
FIG. 10 is a front view of a preferred applicator for use with receptacles having spikes as shown in FIG. 9.

FIG. 10 shows an applicator 620 with handle 622 and an outer plastic package 624. The outer plastic package 624 constitutes one preferred embodiment of a containment means to contain the prepping solution and prevent contamination of the permanent receptacle. The plastic package 624 may be sized to precompress the sponge/pad 626 to a predetermined degree or to enclose the pad 626 without compression (shown without compression in FIG. 10). The plastic package 624 preferably completely encases the entire applicator pad 626 and handle 622, or alternatively it may be open on the handle end. The plastic package 624 may also include one or more tear notches 625 to facilitate opening. Preferably the plastic package 624 is transparent or translucent such that filling of the pad 626 is easily observable.

The plastic package 624 material is preferably selected to ensure a good seal around the spike shown in figures (e.g., spike 604 shown in FIG. 9) when it is inserted into the receptacle 600, and is preferably a polyolefin such as low density polyethylene, linear low density polyethylene, a metallocene polyethylene, polypropylene, a metallocene polypropylene and the like.

Preferably the plastic package 624 has a low coefficient of friction in communication with the receptacle 600 to ensure easy insertion of the applicator pad 626. For example, when the receptacle 600 is high density polyethylene a low density or linear low density polyethylene package 624 is suitable.

The spike 604 is positioned to mate with a slot 628, recess or other means in the applicator to ensure easy insertion of the applicator pad 626. The handle 622 of the applicator 620 preferably has a slot 628 that mates with the spike 604. The tips 630 of the slotted handle 622 are preferably rounded to avoid sharp edges that might other wise cause irritation during use. Other handle configurations are possible such as tubes etc., however, the handle preferably is designed to allow the spike to enter the pad with minimal or no interference.

Figure 11:
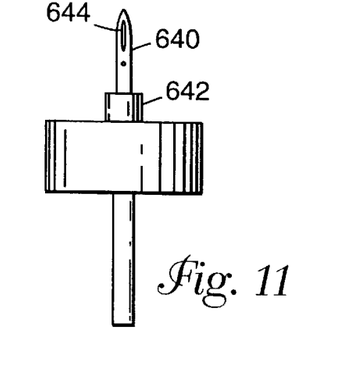
FIG. 11 is a cross section view of another embodiment of the invention which is used with an applicator having a disposable receptacle such as that shown in FIG. 10.

FIG. 11 illustrates an embodiment of the invention in which no permanent receptacle houses the spike 640. Rather, this embodiment relies upon the package and/or a binder to define the amount of solution that the applicator pad is allowed to hold. For example, the containment package may compress the pad into its compressed state, in which the pad will permit less fluid to be loaded into the pad than the pad is capable of holding in its uncompressed state.

The spike 640 of FIG. 11 may optionally have a retractable safety tip that also functions to seal the dispenser when not in use. The base 642 of the spike 640 is preferably flared to ensure a good seal against the containment package. The spike 640 also preferably has holes 644 on its circumference to allow fluid to pass out of the tip in a radial fashion once the dispenser is pressurized. In this manner, such holes 644 (opening through the circumference of the spike) are believed to be less likely to be occluded by sponge material compressed during insertion of the pad into the receptacle than would an axially oriented opening through the tip of the spike 640.

The spike 640 should be fabricated from a relatively rigid material such as metal or high modulus plastics such as polycarbonate, polymethylmethacrylate, ABS, high density polyethylene or filled plastics in order to ensure the pad is easily pierced without deformation and long life of the spike.

The handle 622 of the applicator 620 preferably is not placed completely through the pad 626 and the pad 626 preferably is not slit completely through to accept the handle 622, thus providing pad material at the tip 628 of the handle 622, which is pierced by the spike 640 and thereby helps to ensure a good seal.

To use this kit, the applicator 620 and its containment package 624 (FIG. 10) are pierced over the spike 604 in the receptacle of FIG. 9 down to the base. The dispenser is pressurized, e.g. squeezed, allowing solution to flow up the dip tube and into the resilient pad 626. Once the pad 626 is filled, the dispenser pressure is relieved and any excess solution is sucked back into the bottle. The applicator 620 is then removed from the dispenser spike 604 and taken to the place of use. At this point the plastic outer package 624 is removed and the applicator 620 is ready for use.

Alternatively, the outer plastic package may consist of a thermoformed or otherwise fabricated tray that contains the applicator pad in a first uncompressed state which can be moved to a second compressed state. For example, the pad may be in a first non-compressed zone, moved to a zone suitable for filling where it is compressed. Alternatively, the applicator pad may be filled in a first zone with solution and pulled through a compression device to expel excess solution.

Options where the applicator pad is not shipped in a compressed state are preferred since many pad materials may be prone to taking a compression "set", i.e. if compressed and held for long periods of time they will not rebound to the original precompressed dimensions. In embodiments comprising a containment package with compression, use of a mating dispenser may not be needed but may comprise simply a means for introducing the solution into the containment package. Preferably the dispenser is designed to provide a premeasured volume to the containment means.

In the embodiment of FIG. 9, if the dispenser is pressurized without an applicator pad in place it is possible for solution to enter the receptacle and remain at the bottom of the receptacle. While this may be poured out it creates waste and mess. Therefore, the receptacle preferably further comprises a check valve 610, which closes when the dispenser is pressurized but opens to allow any fluid on the bottom of the receptacle 600 to re-enter the bottle. Opening of the check valve 610 may be accomplished simply by the lower pressure generated once the dispenser is depressurized, i.e. a ball check valve or umbrella check valve.

Figure 12:
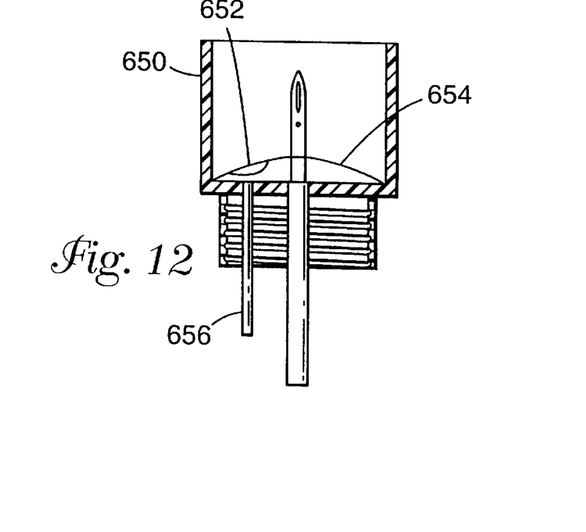
FIG. 12 is a cross section view of another embodiment of the invention which is used with an applicator having a disposable receptacle such as that shown in FIG. 10 with the addition of a liquid return valve actuated by insertion of a applicator.

Preferably, the check valve 610, 652 is provided in an open condition and only closes when the applicator is inserted into the receptacle. In this case the applicator would be adapted to close one or more check valves upon insertion. For example, shown in FIG. 12 is an additional embodiment of the invention wherein a valve 652 is closed upon insertion of the applicator pad. In this design the valve 652 comprises a valve pad attached to a spring 654 which holds the valve 652 in its normally open position. In this manner, if fluid cannot be inadvertently expelled since the bottle cannot be pressurized until the applicator is inserted and closes the valve 652. The preferred valve 652 has a valve spring 654 that biases a valve pad (also 652) adjacent a liquid return channel 656 to open and close the liquid return channel 656.

While FIGS. 9, 11, and 12 show the receptacle spike in a vertical upright position it is understood that other orientations are possible including designs where the applicator pad is inserted and either the pad or spike are moved in order for the spike to engage the applicator pad.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. A kit for applying surgical prepping solution to a patient, the kit comprising:
   an applicator having a resilient, porous pad attached to a handle;
   a bottle for a surgical prepping solution;
   a receptacle attached to the bottle and defining an internal space having a size relative to the pad such that when the pad is placed within the space, the pad is compressed to a predetermined degree;
   a passageway between the bottle and the internal space of the receptacle through which surgical prep solution can flow from the bottle into the internal space to load the pad with surgical prepping solution; and
   a dip tube extending from the receptacle into the bottle, the dip tube defining the passageway as having an inlet near a bottom of the bottle, wherein the dip tube has sides and the dip tube extends into the internal space of the receptacle, the dip tube having outlet slots or holes into the internal space along the sides of the dip tube;
   wherein the pad expands when removed from the internal space.

2. The kit according to claim 1 further comprising means for preventing blockage of the passageway by the pad.

3. The kit according to claim 1 further comprising a flared opening in the receptacle to the internal space.

4. The kit according to claim 1 wherein the bottle and receptacle are blow or vacuum molded in one integral piece.

5. The kit according to claim 1 further comprising a spike within the receptacle for piercing the pad.

6. The kit according to claim 1 further comprising a check valve allowing return of prepping solution to the bottle after the pad of the applicator is removed from the internal space.

7. The kit according to claim 6 wherein the check valve is positioned within the internal space of the receptacle and is normally in an open position preventing pressurization of the bottle until the pad is inserted into the internal space, the check valve being moved to a closed position when the pad is inserted into the internal space.

8. The kit according to claim 1 wherein the pad has a generally polyhedron configuration with two generally parallel major surfaces, the handle being elongate and extending from the pad in a direction generally parallel to the two major surfaces, the internal space of the receptacle having a polyhedron configuration corresponding to the configuration of the pad but smaller than the pad so that the pad is compressed when it is inserted in the internal space.

9. The kit according to claim 8 further comprising a flared opening in the receptacle to the internal space.

10. The kit according to claim 9 further comprising a cap for releaseably sealing the opening in the receptacle, and a tether or hinge connecting the cap to the receptacle.

11. The kit according to claim 1 further comprising disposable packaging enclosing at least the resilient, porous pad of the applicator but not the receptacle or bottle, and a spike within the receptacle for piercing the disposable packaging when the pad is inserted into the internal space of the receptacle to allow prepping solution to load the pad.

12. The kit according to claim 11 wherein the spike has an end, and the handle of the applicator has an enclosed end enclosed within the pad, the enclosed end of the handle being provided with a slot or recess for receiving the end of the spike when the pad is fully inserted into the internal space of the receptacle.

13. The kit according to claim 12 wherein the pad has a generally polyhedron configuration with two generally parallel major surfaces, the handle being elongate and extending from the pad in a direction generally parallel to the two major surfaces, the internal space of the receptacle having a polyhedron configuration corresponding to the configuration of the pad but smaller than the pad so that the pad is compressed when it is inserted in the internal space.

14. The kit according to claim 1 wherein the pad is compressed within the receptacle to between 40–90% of its non-compressed post-wetting volume.

15. The kit according to claim 14 wherein the pad is compressed within the receptacle to between 60–80% of its non-compressed post-wetting volume.

16. The kit according to claim 14 wherein the pad further includes a binder holding the pad in a compressed configuration before the pad is inserted in the receptacle, the binder being selected to allow the pad to expand after it has been loaded with surgical prepping solution.

17. A kit for applying surgical prepping solution to a patient, the kit comprising:
    an applicator having a resilient, porous pad attached to a handle;
    a receptacle adapted to be attached to a bottle of surgical prepping solution, and defining an internal space having a size relative to the pad such that when the pad is placed within the space, the pad is compressed to a predetermined degree;
    a passageway into the internal space of the receptacle through which surgical prep solution can flow from a bottle attached to the receptacle into the internal space to load the pad with surgical prepping solution; and
    a dip tube defining the passageway, the dip tube has sides, the dip tube extending from the receptacle to adapt the dip tube to extend into the bottle, and extending into the internal space of the receptacle, and the dip tube having outlet slots or holes into the internal space along the sides of the dip tube;
    wherein the pad expands when removed from the internal space.

18. The kit according to claim 17 further comprising a flared opening in the receptacle to the internal space.

19. The kit according to claim 17 further comprising a cap for releaseably sealing the opening in the receptacle, and a tether or hinge connecting the cap to the receptacle.

20. The kit according to claim 17 further comprising a spike within the receptacle for piercing the pad.

21. The kit according to claim 17 further comprising disposable packaging enclosing at least the resilient, porous pad of the applicator but not the receptacle or bottle, and a spike within the receptacle for piercing the disposable packaging when the pad is inserted into the internal space of the receptacle to allow prepping solution to load the pad.

22. The kit according to claim 21 wherein the spike has an end and the handle of the applicator has an enclosed end enclosed within the pad, the enclosed end of the handle being provided with a slot or recess for receiving the end of the spike when the pad is fully inserted into the internal space of the receptacle.

23. The kit according to claim 22 wherein the pad has a generally polyhedron configuration with two generally parallel major surfaces, the handle being elongate and extending from the pad in a direction generally parallel to the two major surfaces, the internal space of the receptacle having a polyhedron configuration corresponding to the configuration of the pad but smaller than the pad so that the pad is compressed when it is inserted in the internal space.

24. The kit according to claim 17 wherein the pad has a generally polyhedron configuration with two generally parallel major surfaces, the handle being elongate and extending from the pad in a direction generally parallel to the two major surfaces, the internal space of the receptacle having a polyhedron configuration corresponding to the configuration of the pad but smaller than the pad so that the pad is compressed when it is inserted in the internal space, the receptacle having a flared opening to the internal space.

25. The apparatus according to claim 24 wherein the handle is inserted in the pad a distance of at least 75% of the length of one of the dimensions of the pad.

26. The kit according to claim 24 further comprising a cap for releaseably sealing the opening in the receptacle, and a tether or hinge connecting the cap to the receptacle.

27. The kit according to claim 17 wherein the receptacle includes means for releasably attaching the receptacle to a bottle.

28. The kit according to claim 27 wherein the pad is compressed within the receptacle to between 40–90% of its non-compressed post-wetting volume.

29. The kit according to claim 28 wherein the pad is compressed within the receptacle to between 60–80% of its non-compressed post-wetting volume.

30. The kit according to claim 29 wherein the pad further includes a binder holding the pad in a compressed configuration before the pad is inserted in the receptacle, the binder being selected to allow the pad to expand after it has been loaded with surgical prepping solution.

31. An apparatus for applying a liquid to an applicator having a resilient, porous pad, the apparatus comprising:
  a receptacle having an internal space such that when the pad is placed within the space, the pad is compressed to a predetermined degree;
  a bottle containing surgical prepping solution; and
  an inlet tube having sides, the inlet tube extending into the internal space, the inlet tube defining a passageway in fluid communication with the bottle for dispensing surgical prepping solution into the pad while the pad is within the receptacle, the inlet tube having outlet slots into the internal space along the sides of the inlet tube.

32. The apparatus according to claim 31 wherein the bottle and receptacle are blow or vacuum molded in one integral piece.

33. The apparatus according to claim 31 wherein the inlet tube extends in one direction into the internal space and in the opposite direction into the bottle, the inlet tube having an inlet near the bottom of the bottle.

34. The apparatus according to claim 33 wherein the pad is compressed within the receptacle to between 40–90% of its non-compressed post-wetting volume.

35. The apparatus according to claim 34 wherein the pad is compressed within the receptacle to between 60–80% of its non-compressed post-wetting volume.

36. A method of preparing a patient for surgery, the method comprising the steps of:
  (a) providing an applicator having a resilient, porous pad with a saturation level, and an apparatus comprising:
    a receptacle having an internal space such that when the pad is placed within the space, the pad is compressed to a predetermined degree; and
    a passageway into the receptacle for dispensing a surgical prepping solution onto the pad while the pad is within the receptacle;
  (b) inserting the pad into the internal space of the receptacle, and compressing the pad to a predetermined degree within the internal space;
  (c) either before or after step (b), passing surgical prepping solution through the passageway into the internal space of the receptacle, wherein upon completion of steps (b) and (c) the pad is wetted with surgical prepping solution;
  (d) withdrawing the pad from the receptacle such that the pad expands sufficiently so that the surgical prepping solution occupies less than the saturation level of the pad; and
  (e) painting the surgical prepping solution onto the patient with the applicator.

37. The method according to claim 36 wherein the step of compressing the pad to a predetermined degree within the internal space comprises compressing the pad within the receptacle to between 40–90% of the pad's non-compressed post-wetting volume.

38. The method according to claim 36 wherein the step of compressing the pad to a predetermined degree within the internal space comprises compressing the pad within the receptacle to between 60–80% of the pad's non-compressed post-wetting volume.

39. The method according to claim 38 further comprising the following steps:
  holding the pad in a compressed configuration with a binder before the pad is inserted in the receptacle; and
  dissolving, eroding, swelling or otherwise releasing the binder with the surgical prepping solution to allow the pad to expand after it has been loaded with surgical prepping solution to prevent reuse of the pad in internal space of the receptacle.

40. The method according to claim 38 further comprising the following steps:
  connecting a cap to the receptacle to releaseably seal the internal space of the receptacle; and
  closing and opening the internal space of the receptacle with the cap.

41. A kit for applying surgical prepping solution to a patient, the kit comprising:
  an applicator having a resilient, porous pad attached to a handle;

a containment package defining an internal space having a size relative to the pad such that when the pad is placed within the space, the pad is compressed to a predetermined degree;

a receptacle, and a spike within the receptacle for piercing the containment package, the spike having an internal lumen in fluid communication with a source of surgical prepping solution, and an opening into the lumen such when the spike pierces the containment package, prepping solution may be loaded into the pad;

wherein the pad expands when the containment package is removed from the pad.

42. The kit according to claim 41 wherein the opening is formed along the circumference of the spike adjacent its tip; the handle of the applicator having an enclosed end enclosed within the pad, the enclosed end of the handle being provided with a slot or recess for receiving the tip of the spike.

* * * * *